(12) United States Patent
Peled et al.

(10) Patent No.: US 11,229,722 B2
(45) Date of Patent: Jan. 25, 2022

(54) SYSTEM AND METHOD FOR HARVESTING AUTOLOGOUS ADIPOSE TISSUE

(71) Applicants: Omer Peled, Haifa (IL); A. Jason Mirabito, Portsmouth, NH (US)

(72) Inventors: Omer Peled, Haifa (IL); A. Jason Mirabito, Portsmouth, NH (US)

( * ) Notice: Subject to any disclaimer, the term of this patent is extended or adjusted under 35 U.S.C. 154(b) by 196 days.

(21) Appl. No.: 16/259,863

(22) Filed: Jan. 28, 2019

(65) Prior Publication Data
US 2019/0336646 A1 Nov. 7, 2019

Related U.S. Application Data

(60) Provisional application No. 62/623,385, filed on Jan. 29, 2018.

(51) Int. Cl.
*A61M 1/00* (2006.01)
*A61M 5/19* (2006.01)
(Continued)

(52) U.S. Cl.
CPC ....... *A61L 27/3691* (2013.01); *A61L 27/3804* (2013.01); *A61L 27/3834* (2013.01);
(Continued)

(58) Field of Classification Search
CPC ............. A61L 27/3691; A61L 27/3834; A61L 27/3804; A61M 1/0001; A61M 5/19; A61M 2202/08; A61M 1/67; A61M 1/88; A61M 5/31596; A61M 2005/31598; A61M 1/029; A61M 1/0295; A61M 1/3693; A61M 1/3695; A61M 1/3696; A61M 1/3698
See application file for complete search history.

(56) References Cited

U.S. PATENT DOCUMENTS 3,660,037 A * 5/1972 Sokol ..................... G01N 15/05
422/73
4,373,535 A * 2/1983 Martell ............... A61B 5/15003
600/578
(Continued)

*Primary Examiner* — Adam Marcetich
(74) *Attorney, Agent, or Firm* — ISUS Intellectual Property PLLC; Anthony Jason Mirabito

(57) ABSTRACT

A triple-chambered container includes: a main container body with a first chamber which has an opening at its distal end; a main barrel formed and movable longitudinally within the first chamber, the main barrel defining therein a second chamber for receiving fluids, the main barrel further having an apertured stopper at its distal end; a second barrel formed within the main barrel, the second barrel defining a third chamber for receiving fluids, the second barrel being movable longitudinally within and with respect to the main barrel, the second barrel having a distal end which is engageable and disengageable with the apertured stopper; a shaft adapted to fit within the second barrel, the shaft being movable longitudinally within and with respect to the second barrel, the shaft having a distal end which is engageable and disengageable with an aperture in the second barrel; a device for controlling engaging and disengaging of the distal end of the shaft with the aperture of the second barrel. The first chamber, the second chamber and the third chamber may be selectively moved to receive and discharge fluids with respect to one another.

2 Claims, 10 Drawing Sheets

(51) Int. Cl.
*A61L 27/36* (2006.01)
*A61L 27/38* (2006.01)

(52) U.S. Cl.
CPC ............ *A61M 1/0001* (2013.01); *A61M 5/19* (2013.01); *A61M 2202/08* (2013.01)

(56) References Cited

U.S. PATENT DOCUMENTS

| | | | | |
|---|---|---|---|---|
| 5,858,253 | A * | 1/1999 | Holm | B01L 3/5021 210/702 |
| 5,873,841 | A * | 2/1999 | Brannon | A61B 5/155 600/578 |
| 6,086,559 | A * | 7/2000 | Enk | A61M 5/482 604/121 |
| 6,716,187 | B1 * | 4/2004 | Jorgensen | A61M 1/029 206/223 |
| 2006/0273050 | A1 * | 12/2006 | Higgins | G01N 33/491 210/787 |
| 2007/0208321 | A1 * | 9/2007 | Leach | B01L 3/50215 604/500 |
| 2008/0146917 | A1 * | 6/2008 | Freund | B01D 21/0012 600/431 |
| 2008/0166421 | A1 * | 7/2008 | Buhr | A61K 35/18 424/530 |
| 2011/0284460 | A1 * | 11/2011 | Leach | B01L 3/50215 210/513 |
| 2011/0309037 | A1 * | 12/2011 | Lee | A61M 5/3145 210/781 |
| 2012/0009588 | A1 * | 1/2012 | Rajagopal | B01L 3/5082 435/6.15 |
| 2013/0068676 | A1 * | 3/2013 | Leach | G01N 33/491 210/123 |
| 2014/0276386 | A1 * | 9/2014 | Mansour | A61J 1/2096 604/93.01 |
| 2015/0064687 | A1 * | 3/2015 | Nemirovsky | A61M 1/029 435/2 |
| 2016/0298076 | A1 * | 10/2016 | Centeno | C12N 5/0663 |
| 2017/0000826 | A1 * | 1/2017 | Tucker | A61M 1/029 |
| 2017/0368226 | A1 * | 12/2017 | Pilkington | A61L 27/3604 |
| 2018/0010086 | A1 * | 1/2018 | Gupta | B01D 17/0214 |
| 2019/0134565 | A1 * | 5/2019 | Wang | B01D 63/16 |
| 2020/0330269 | A1 * | 10/2020 | Bley | A61F 9/0017 |

\* cited by examiner

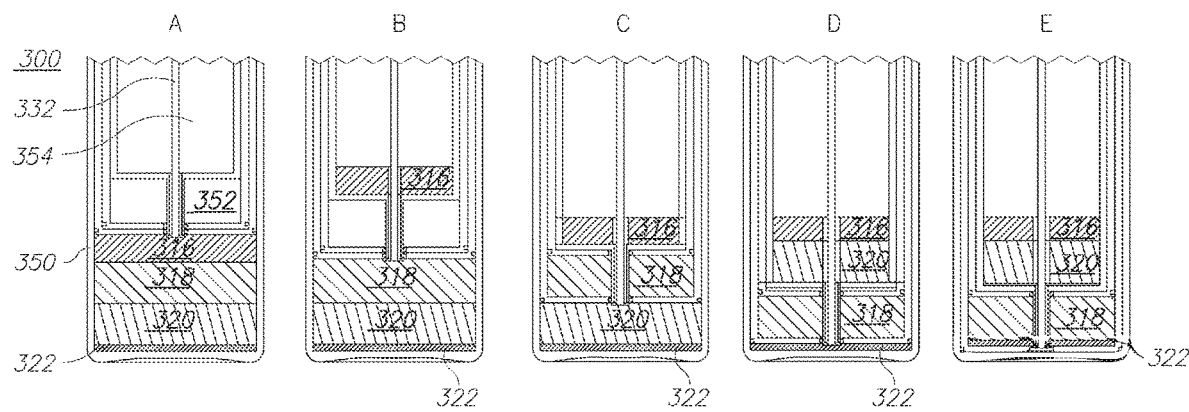
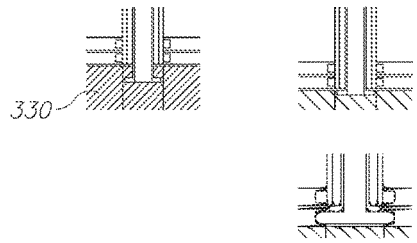
FIG.8A  FIG.8B  FIG.8C  FIG.8D  FIG.8E

SYSTEM AND METHOD FOR HARVESTING AUTOLOGOUS ADIPOSE TISSUE

RELATED APPLICATIONS

This application is related to and claims priority to U.S. provisional application Ser. No. 62/623,385, filed Jan. 29, 2018, the entire contents of which is herein incorporated by reference.

BACKGROUND OF THE PRESENT INVENTION

In the medical aesthetics field, many techniques are known and practiced to lessen skin tissue imperfections such as wrinkles and sagging skin, particularly in the facial areas. Many of these involve chemical treatments, such as chemical peels, or the use of electromagnetic energy, such as lasers, or even the introduction of somewhat poisonous materials such as Botox® which may be injected into the skin to "plump up" that area of the skin tissue.

It is also known to harvest, filter and inject autologous adipose tissue from one portion of the body and to reinject the filtered fat into a desired area such as in the area of wrinkles or sagging tissue. The benefit of using this autologous fat is that the probability of rejection by the person's immune system is very much lessened if not eliminated altogether.

Known techniques, however, are cumbersome, complicated and expensive. Further, with existing techniques, the need to remove and move fat components during the harvesting and filtering process may cause contamination of the fat components and thus medical complications to the patient.

Thus, there is a need for simple, inexpensive device that in addition avoids contamination problems by limiting or eliminating exposure to fat cell components all within one device. It is to this realization that the present invention is directed.

In addition, it has been found that in existing autologous fat removal systems, methods and devices that the rejection rate may be unacceptably high. This has been researched and theorized to be due to the relative absence of growth factors in the fat removed and filtered. (See, Tan S S, Ng Z Y, Zhan W, Rozen W. Role of Adipose-Derived Stem Cells in Fat Grafting and Reconstructive Surgery. J. Cutan Aesthet Surg [serial online] 2016 [cited 2018 Jan. 12]; 9:152-6). This article discusses the separation and addition of adipose-derived stem cell (ASC) rich component of stromal vascular fraction to, which exists in the lipoaspirate, to the reinjected autologous fat. One existing problem is how to structure a device and its method of use to separate out the several fat components and to mix the ASC material with the adipose tissue efficiently and without risking contamination. It is to this realization that the present invention is also directed.

SUMMARY OF THE PRESENT INVENTION

In an aspect, a triple-chambered container includes: a main container body with a first chamber which has an opening at its distal end; a main barrel formed and movable longitudinally within the first chamber, the main barrel defining therein a second chamber for receiving fluids, the main barrel further having an apertured stopper at its distal end; a second barrel formed within the main barrel, the second barrel defining a third chamber for receiving fluids, the second barrel being movable longitudinally within and with respect to the main barrel, the second barrel having a distal end which is engageable and disengageable with the apertured stopper; a shaft adapted to fit within the second barrel, the shaft being movable longitudinally within and with respect to the second barrel, the shaft having a distal end which is engageable and disengageable with an aperture in the second barrel; a device for controlling engaging and disengaging of the distal end of the shaft with the aperture of the second barrel. The first chamber, the second chamber and the third chamber may be selectively moved to receive and discharge fluids with respect to one another.

In another aspect, the triple-chambered container is adapted for withdrawal of human adipose tissue, separation of adipose tissue components and reintroduction of specified adipose tissue components into a skin tissue of a human body.

In yet another aspect, the main container cooperates with a harvesting system which may include a suction device for removing fat tissue from the body into a cannula or other tube-like device that then is fed to the container. The container may also cooperate with a dispensing system, pressure-fed or otherwise, that, after separation of the fat from other components as described herein, dispenses the fat to, for example, a needle at its distal end, the needle being used to inject the fat from the container into a skin tissue of a human body.

In a yet further aspect, a method of capturing and separating adipose tissue components includes:

(a) providing the triple-chamber container described;

(b) providing a volume of adipose tissue to the first chamber;

(c) centrifuging the container so that the adipose tissue is separated into four components;

(d) the four components being, in order: oils, fat, blood components, and adipose-derived stem cells;

(e) moving the oils into third chamber by moving the shaft to open opening and moving the main barrel in the direction of the distal end of the outer chamber until the oils are contained in the inner barrel;

(f) closing the opening such that the oils are constrained to remain within the third chamber;

(g) moving the fat into the second chamber by moving the second barrel in a proximal direction, thus opening the apertured stopper, then advancing the main barrel in a distal direction so that the fat enters into second chamber;

(g) closing the apertured stopper with the second barrel such that the fat is constrained to remain within the second chamber;

(h) moving the blood components into third chamber by moving the shaft to open opening and moving the main barrel in the direction of the distal end of the outer chamber until the blood components are contained in the inner barrel with the oils;

(i) closing the opening such that the blood components and the oils are constrained to remain within the third chamber; and, (j) moving the adipose-derived stem cells into the second chamber by moving the second barrel in a distal direction, to move the adipose-derived stem cells, after having opened the apertured stopper, present in the main chamber into the second chamber. Alternatively, the operator may move the fat cells from the second chamber to the main chamber, in which case the main chamber may act as the "working" chamber from which the autologous material will be applied to the skin tissue In another aspect of the method, the method includes:

(k) moving the fat and the adipose-derived stem cells from the second chamber into the first chamber;

(l) closing the aperture stopper after the fat and the adipose-derived stem cells have been moved into the first chamber; and, (m) moving the main barrel in a distal direction to expel the fat cells and the adipose-derived stem cells from the first chamber to outside the first container for injection into a human body.

BRIEF DESCRIPTION OF THE DRAWINGS

FIGS. 8A-8E illustrate a process, in another embodiment, of the separation of adipose fat materials into several component materials.

DETAILED DESCRIPTION OF THE PRESENT INVENTION

Figure 1:
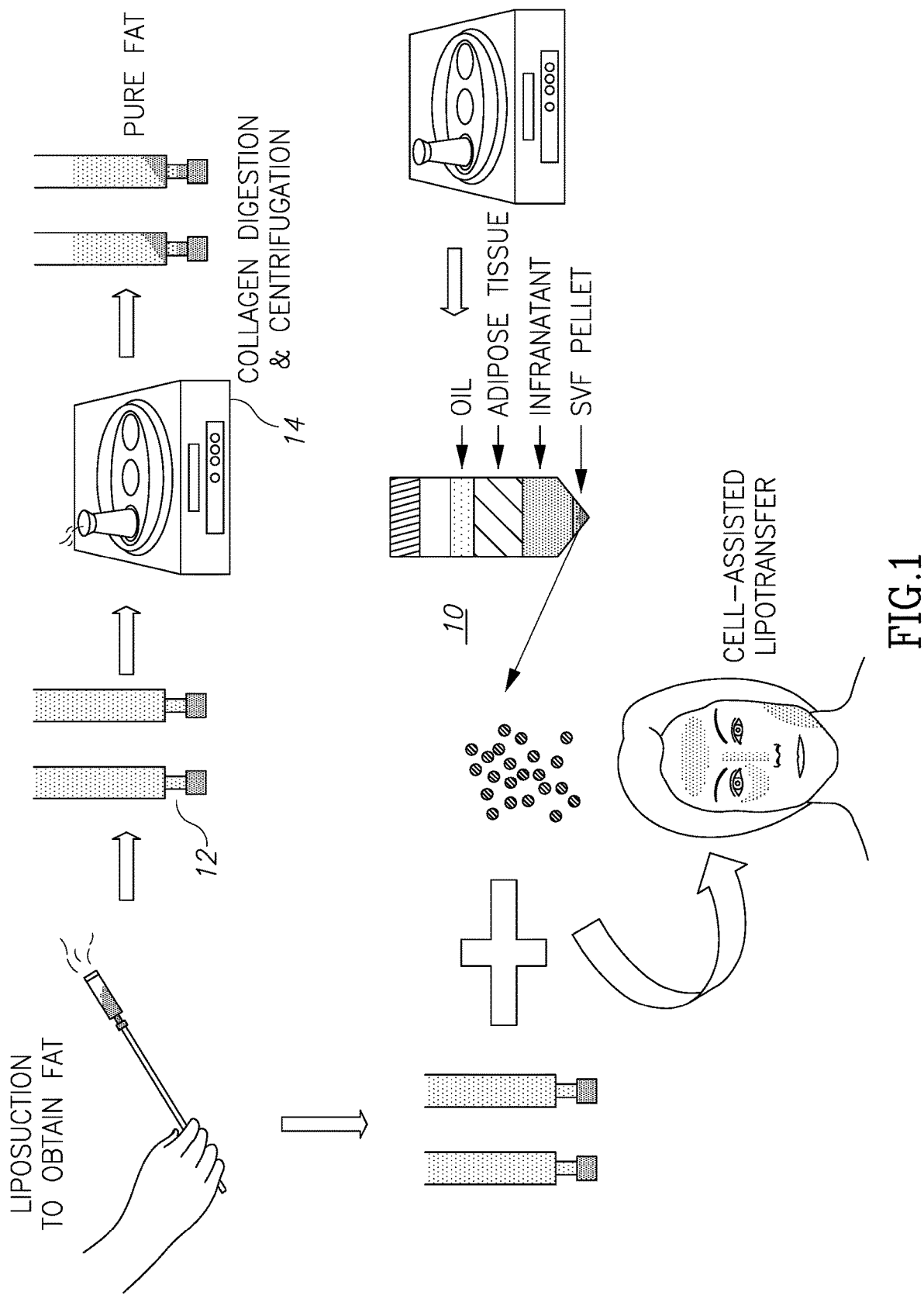
FIG. 1 illustrates a flow chart type sequence of a process in connection with the present invention.
Figure 2:
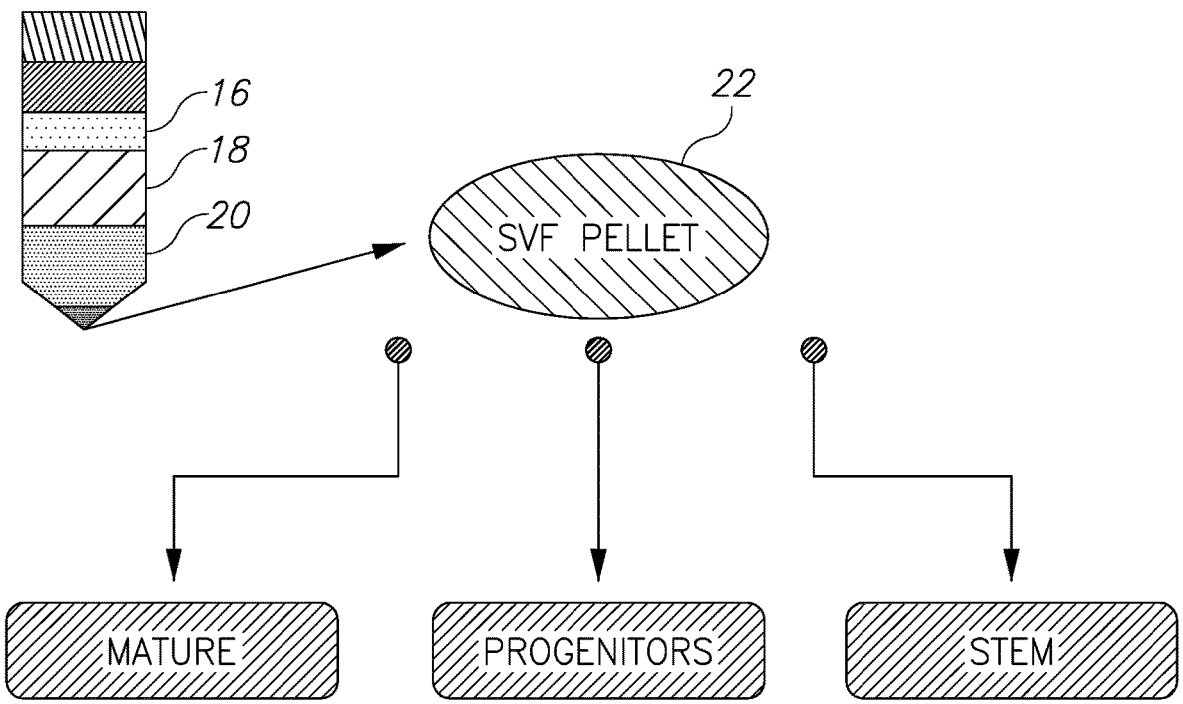
FIG. 2 illustrates the resulting separation of fluids following centrifugation of removed adipose fat materials.

Turning now to FIGS. 1 and 2, these figures (taken from the above-cited Tan et al. article) illustrate the general known process of harvesting and filtering adipose tissue and are self-explanatory. What is significant to note is the illustrated levels of material 10 shown in those figures. This separation of components comes about after centrifugation of the tubes 12 in the centrifuge 14. Of these materials, the desired reinjected material is a mix of the purified components which are located at levels 18 (the adipose tissue) and 22 (the SVF pellet or adipose-derived stem cells), although sometimes only the adipose tissue separation material may be desirable. The problem, of course, is how to separate the desirable components, such as 18 and 22, from the not-needed components like 16 (oils and lipids) and 20 (infranatant), and not allowing intermixing of desirable and not-needed components, all within an environment so as to prevent contamination.

Figure 3A:
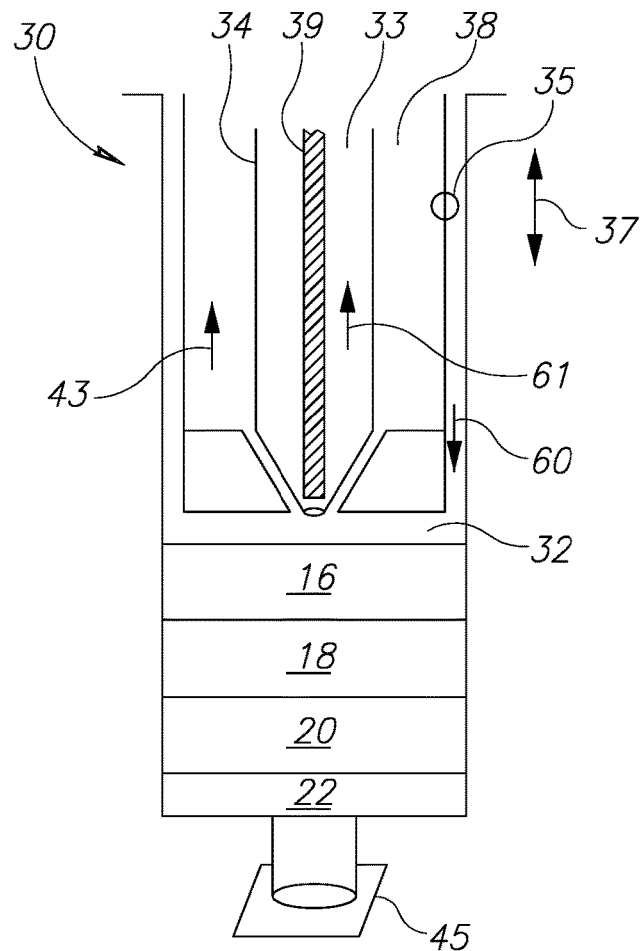
FIGS. 3A through 3D illustrate the structure of the container of FIG. 4 and the process of separation of adipose fat materials into several components.
Figure 3A:
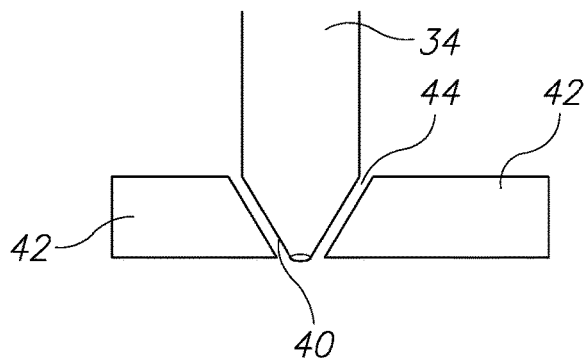
Figure 3A:
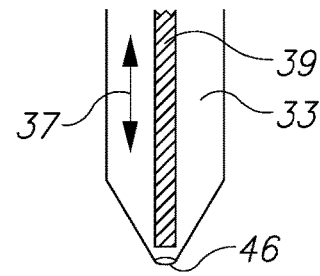
Figure 3B:
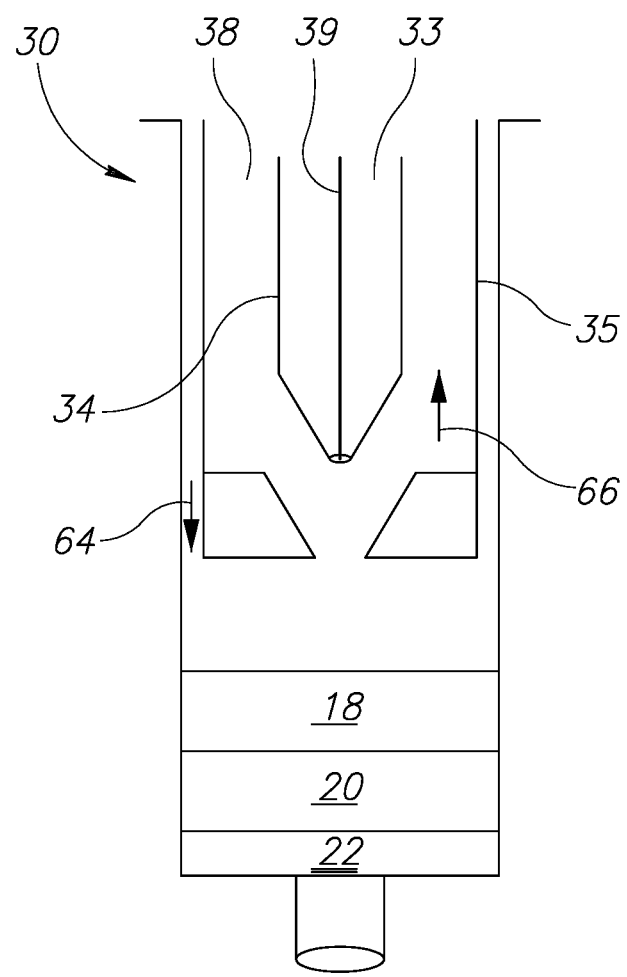

Turning now to the operation of the container of the present invention in separating various components of excised adipose fat, in a first step the container of the present invention (or another container for that matter) may be fitted with an appropriate needle at its distal end, the needle introduced into a fatty region in a person's body as is well known and the main plunger moved to suck fat and other tissue components into the main volume (or main container) 32 of the container shown in FIG. 3A.

After removing a given and selected amount of fat tissue into the volume 32, as shown at 12 in FIG. 1, the container itself or fat in a separate vial is placed into the centrifuge 14 and spun for the requisite amount of known in the art to separate the components as shown at 10 in FIG. 1 and in FIG. 2, where the components are noted as components 16, 18, 20 and 22.

As discussed above, the desirable components for infusion back into the patient are components 18 and 22, that is, "pure" fat 18 and SVF 22, or just the fat 18 alone. The process in the case of separating the components and reuniting components 18 and 22 is as follows.

The separation of components is more complicated due to the fact that the "desirable" component or components are either not contiguous to one another plus the fact that the "desirable" components may be bounded or surrounded by components that are less or not at all desirable. It's not a simple task of dumping one of the components from the container by pushing in a plunger. Also, the desire is to not expose components to the outside world to avoid contamination, which is a distinct possibility if, for example, the plunger is removed and another container is used to remove, for example, the oils component 16 from the container.

Two-barrel syringes are known, employing a main barrel and an inner barrel, such as is shown and described in literature associated with the Arthrex ACP double container system. Even with this type of container, separating out components of autologous fat without exposure to the outside world is difficult if not impossible.

Turning now to FIGS. 3A to 3D, these figures illustrate the components of a triple barrel container that is suited to perform the separation and filtering of adipose tissue components all within the device itself to cause a mixture of the adipose tissue component 18 and the SVF component 22 that will then be injected into the target tissue.

FIG. 3A illustrates the various components of the container 30. The container 30 has a main container barrel interior space 32. A main plunger 35, movable in directions 37 within the main barrel volume 32, is itself substantially hollow on its inside as shown by the volume 38 but includes a second plunger 34 such that the usable volume of the volume 38 to hold fluids in the space surrounding the second plunger 34. The second plunger 34 is itself movable within the volume 38 in the same directions 37 as main plunger 35. The second plunger 34 has a hollow volume 33 which may be used to hold fluids as will be explained below. The hollow volume 33 receives a shaft 39. Shaft 39 is also movable within second plunger 34 in the same directions 37.

As shown in FIG. 3A', the distal end 40 of the second plunger 34 may be tapered to fit into base 42 at the distal end of the main plunger 35. The base 42 may be in the form of an aperture rubber-like stopper with a central through-hole or an opening 44. The base 42 may be shaped to compliment and mate with the shape of the distal end 40. Since the second plunger 34 can move in directions 37, it will be seen that the distal end 40 can be positioned so as to seal off the hollow volume 38 or to allow communication of fluids to and from the barrel interior space 32 into or out of volume 38.

In addition, as shown in FIG. 3A", the shaft 39 is movable in directions 37 in such a way that it may close or open aperture 46 to control the ingress and egress of fluids which may be present in volume 33.

Thus, the container has at least three separate volumes which can be isolated or open to the ingress or egress of liquids. There is a main volume 32 which can be increased in volume and decreased in volume to receive or discharge liquids as main plunger 35 is sealingly moved in directions 37. There is also a volume 38 formed within main plunger 35 surrounding second plunger 34 that may accept or discharge liquids in volume 38 either from or to main volume 32 depending on the position of the distal end 40 in relation to the base 42. Finally, there is a volume 33 that can accept or discharge liquids from or to main volume 32 through action of the shaft 39. Each of the plungers 35 and 34 and the shaft 39 are movable independent of one another to selectively hold, take in or express fluids into and out of the volumes 32 or 38 or 33 as desired.

Thus, there is disclosed a container that possesses three separate and separable volumes. Of course, additional volumes can be created using similar principles and structures to create quadruple volume containers and so on.

Turning now to the operation of the container of the present invention in separating various components of excised adipose fat, in a first step the container 30 of the present invention (or another container for that matter) may be fitted with an appropriate needle at its distal end or a dedicated harvesting system which may include an aspirating cannula connected to a vacuum port and/or an irrigation port as known in the fat harvesting industry, the needle or the harvesting system introduced into a fatty region in a person's body as is well known and the main plunger 35 moved in direction 43 to suck fat into the volume 32. Alternatively, main plunger 35 may already be in a withdrawn position so that volume 32 is ready to accept harvested material from the harvesting system by using an alternative vacuum channel.

After removing a given and selected amount of fat tissue into the volume 32, as shown at 12 in FIG. 1, the container itself (or the fat components in a separate vial or tube) is placed into the centrifuge 14 and spun for the requisite amount of known in the art to separate the components as shown at 10 in FIG. 1 and in FIG. 2, where the components are noted as components 16, 18, 20 and 22. Alternatively, the container itself may be positioned already in a spinning system inside a main counsel which is designed to spin the container once the harvesting has been completed.

As discussed above, the desirable components for infusion back into the patient are components 18 and 22, that is, "pure" fat 18 and SVF 22, or just the fat 18 alone. The process in the case of separating the components and reuniting components 18 and 22 is as follows and may be done manually or by a dedicated automated system:

Turning again to FIG. 3A, the components 16, 18, 20 and 22 are shown as having been already introduced into the main container volume 32 and having been through the centrifuging process so that there are 4 distinct layers formed. The distal end of the container may be sealed with stopper 45. In FIG. 3A, the main plunger 35 may be moved in direction 60 toward contact with the upmost fluid 16 before the first step.

The first desired step is to get rid of the oils component 16. In this part of the separation process, the distal end of shaft 39 is disengaged from the aperture 46 by moving the shaft 39 in the direction 61, so that fluids are able to enter into volume 33. The main plunger 35 is moved in direction 60 and contacts the upper surface of the level 16 so that the oils fluid 16 will enter into and be held in volume (chamber) 33. It should be mentioned that at this stage main plunger 35 is moved in direction 60 together with second plunger 34 in such a way that distal end 40 seals opening 44 in base 42. The shaft 39 is then moved in the direction opposite to direction 61 so that the shaft engages and seals aperture 46 (FIG. 3A"). The volume 33 is then in a closed state. Other than when fluids are either being introduced into the main container body or being expelled, the stopper 45 remains screwed onto the distal end of the container to seal it as well as to permit fluids to move into and out of the chambers (volumes) in the container. Thus, stopper 45 is screwed onto the distal end of the container as the main plunger 35 is moved in direction 60. Otherwise, of course, fluids 16, 18, 20 and 22 would exit from the volume 32.

At this juncture, the oils/fluids 16 are captured and sealed within volume 33 and the next level (down as in the drawing) of fluids is the fat tissue in level 18. Next, as in FIG. 3B, the main plunger 35 is shown in contact with the top level of layer 18 after the material 16 has been moved into the 33.

The second plunger 34 is moved in direction 66 so that the distal end 40 moves out of sealing contact with base 42. This creates opening 44 (FIG. 3A') so that the fat fluid can move into the volume 38 by pushing main plunger 35 in a distal direction. At this time, the volume 33 has been already sealed so that nothing enters it at this stage. So, at this point oil fluids 16 are contained in volume 33 and fat fluid 18 is now contained in volume 38.

At this point, there remain only fluids 20 and 22 in the main volume 32. Fluid 20 is not needed or desired and must be somehow removed to be discarded. Fluid 22 is a fluid that may be kept and combined with fluid 18, as explained above.

Figure 3C:
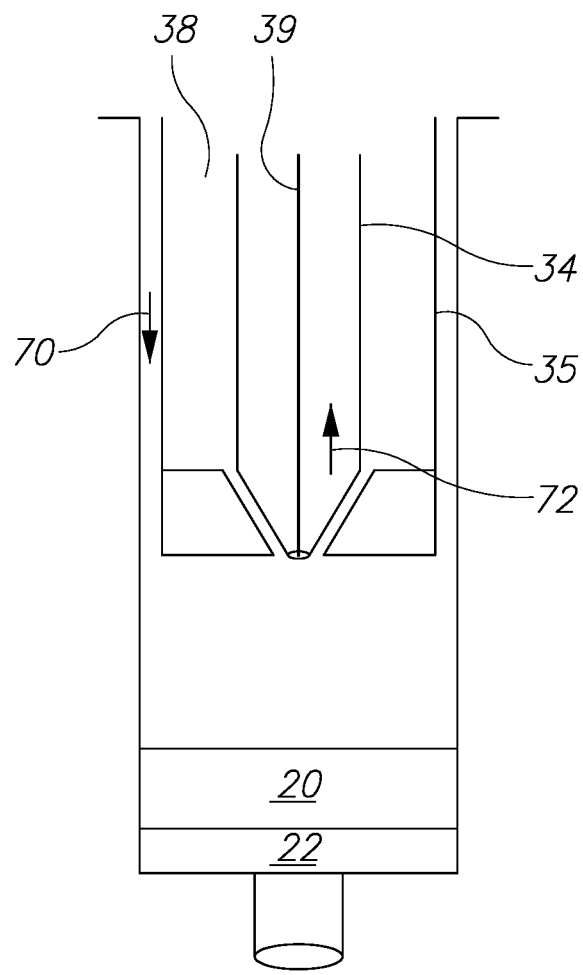

Next, and turning to FIG. 3C, the main plunger 35 is contact in with the top level of fluid 20. The next step is move fluid 20 into volume 33 which already contains fluid 16. The shaft 39 is moved in direction 72 so that it assumes the position shown in FIG. 3A". It is now open to accept fluid 20 within volume 33, but volume 38 is sealed so that no fluid may enter it. As the plunger 35 is moved down, the fluid 20 enters volume chamber 33 to join with fluid 16 from a previous step. These two fluids will be discarded so their presence mixed together in the same volume 33 is not relevant.

Figure 3D:
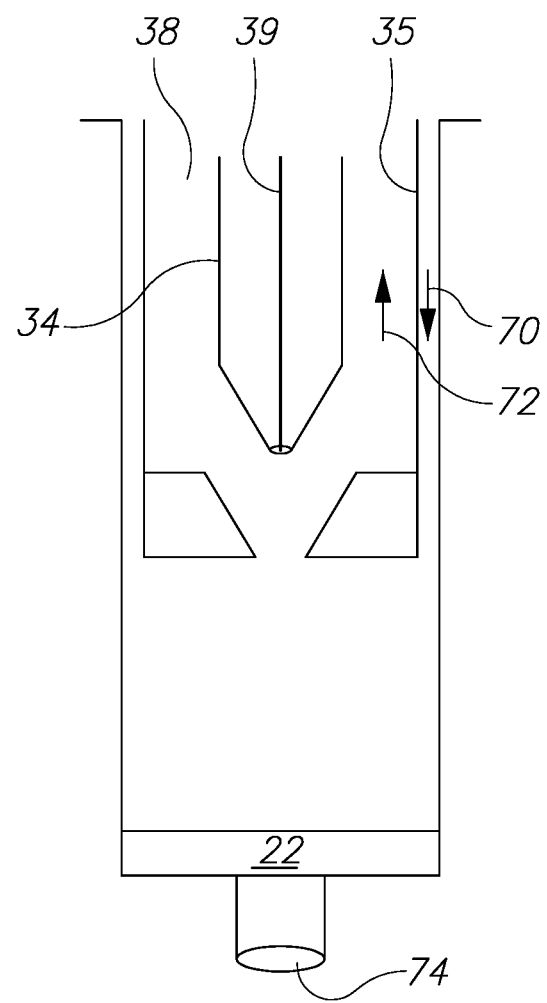

Finally, turning to FIG. 3D, the plunger 34 is moved in direction 70, and the main plunger 35 moved in direction 72 to contact and receive fluid 22 within the volume chamber 38 which already contains the fluid 18. The chamber 38 is then sealed. At this point the desirable fluids 18 and 22 are mixed and contained in volume 38 and ready to be reinjected into the patient's body. Alternatively, instead of adding fluid 22 from chamber 32 into fluid 18 in chamber 38 by positive pressure, fluid 18 from chamber 38 may be added into fluid 22 in chamber 32 by negative pressure. Once mixed, the mix can be injected into the patient as described below.

When ready to be reinjected into the patient, the second plunger 34 is moved in first in direction 70 to assume the position shown in FIG. 3A'. At time the stopper 45 is in place on the distal end of the container. Then main plunger 35 is moved in direction 70 so that fluids 18 and 22 by force of vacuum (because the stopper 45 is mounted on the distal end of the container) are moved out of volume 38 and into main container volume 32. Then the volume 38 is sealed with the distal end of the second plunger 34 engaging the surface 42. At this juncture, the fluids 18 and 22 are within the main volume 32 and ready to be reinjected. Next, main plunger 35 is moved in direction 72 (with stopper 45 removed) so that the combined fluids 18 and 22 pass through opening 74, through an injection needle or a grafting system (not shown) and into the patient's body. The container containing fluids 16 and 20 in volume chamber 33 can then be discarded.

While the above description explains segregation of 4 layers of fluids, the structure of the container allows, for example, by changing the methodology, separating less than 4 and/or greater than 4 layers of fluid. If, for example, only the fat layer is desired to be reinjected, during the part of the process described above when the fluid 20 is removed, the plunger can be further advanced to take into the chamber fluid in level 22 as well.

Also, while the operation of the container of the present invention has been shown largely from the viewpoint of the distal portion of the container, there are mechanisms not shown but known in the art that act, for example, to move the plunger 35, the second plunger 34 and the shaft 39 in directions, for example, 70 and 72, by manipulating a device at the proximal end of the container body 30.

Figure 4:
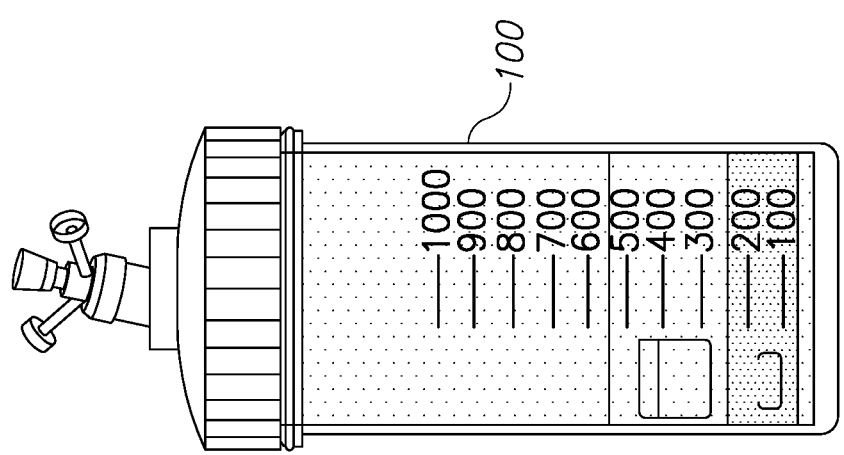
FIG. 4 illustrates an embodiment of a container for receiving and separating adipose fat materials into its several components.

Turning now to FIG. 4, that figure shows a container that may be suitable for adipose tissue separation in connection with the present invention. The container 100 may be of any desired volume depending on the amount of adipose tissue to be harvested from the patient. For example, the amount of adipose tissue for "filling" facial wrinkles will likely be less than the amount for breast augmentation or repair. The container 100 may also be of any suitable shape to suit the separation of adipose materials.

Figure 5:
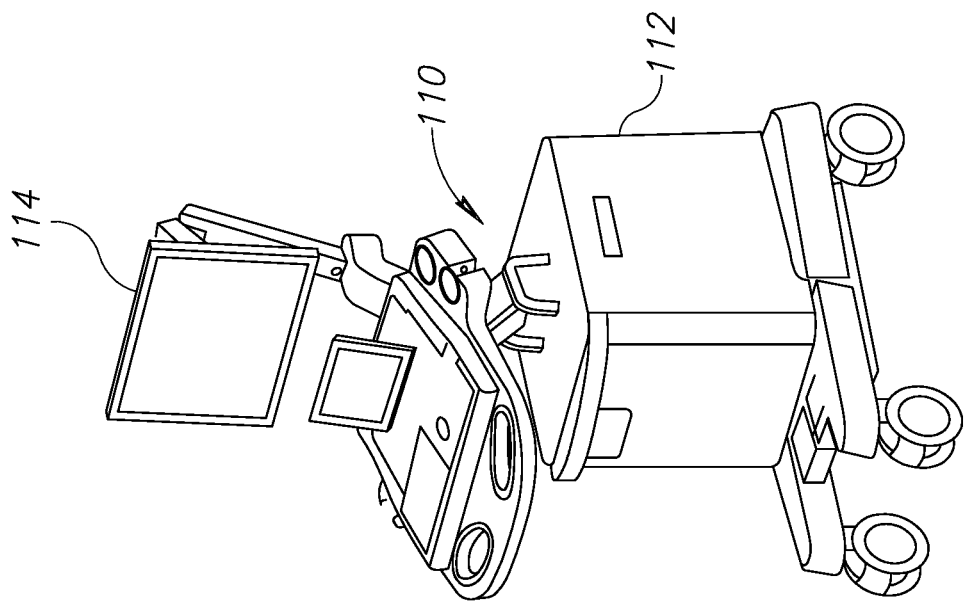
FIG. 5 illustrates a console and system for controlling the centrifugation, separation and introduction of adipose tissue and stem cells into a body.

FIG. 5 illustrates a general form of a console and device 110 for automated or semi-automated control of adipose tissue separation. The console may contain a portion 112 into which the container 100 may be inserted for centrifugation and then separation of component materials as described herein and below in connection with FIG. 6. The portion 112 may therefore contain a centrifuge device, as well as mechanical or other mechanisms to separate the components of the adipose tissue, suitable controls for such mechanism or mechanisms, a programmable controller to control the operation of the device or console 110, as well as a GUI 114 through which an operator may control the sequence of harvesting the adipose tissue, separating the adipose material into several components, removing undesired components, and finally introducing selected components into the patient's body.

Figure 6:
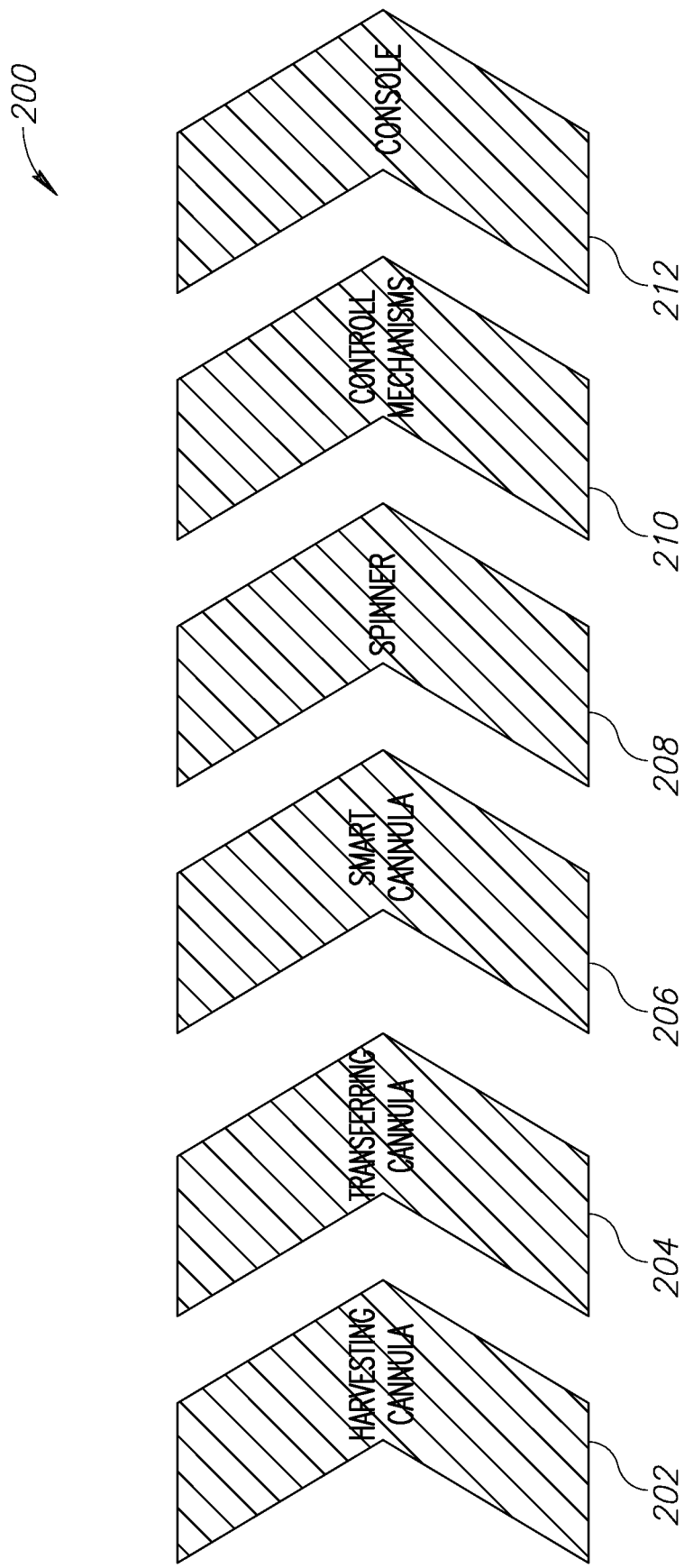
FIG. 6 illustrates the separation of adipose fat materials into several components.

FIG. 6 illustrates 200 the operation of the present invention, starting from harvesting the adipose tissue components in connection with the console of FIG. 5. In an embodiment, a harvesting cannula first harvests adipose tissue in step 202 from the patient. This may be incorporated into the console 110 or be a separate unit. A transferring cannula unit 204 may be used to reintroduce selected adipose tissue components back into the patient. Like the cannula 202, the cannula 204 maybe incorporated into the console 110 of be a separate unit. A smart container 206 may be a container such as container 100 shown in FIG. 4. Such container may be preferably insertable into or contained within console 110. The spinner 208, or other device which separates the adipose tissue into several components, such as a centrifuge, may preferably be incorporated into console 110 or be a separate unit. Mechanisms that control the spinning or centrifugation of adipose material and operate the separation sequence described herein may include various pressure, electrical or pneumatic devices 210, all of which are controlled 212 from a console (such as console 110) through a GUI 114.

Figure 7:
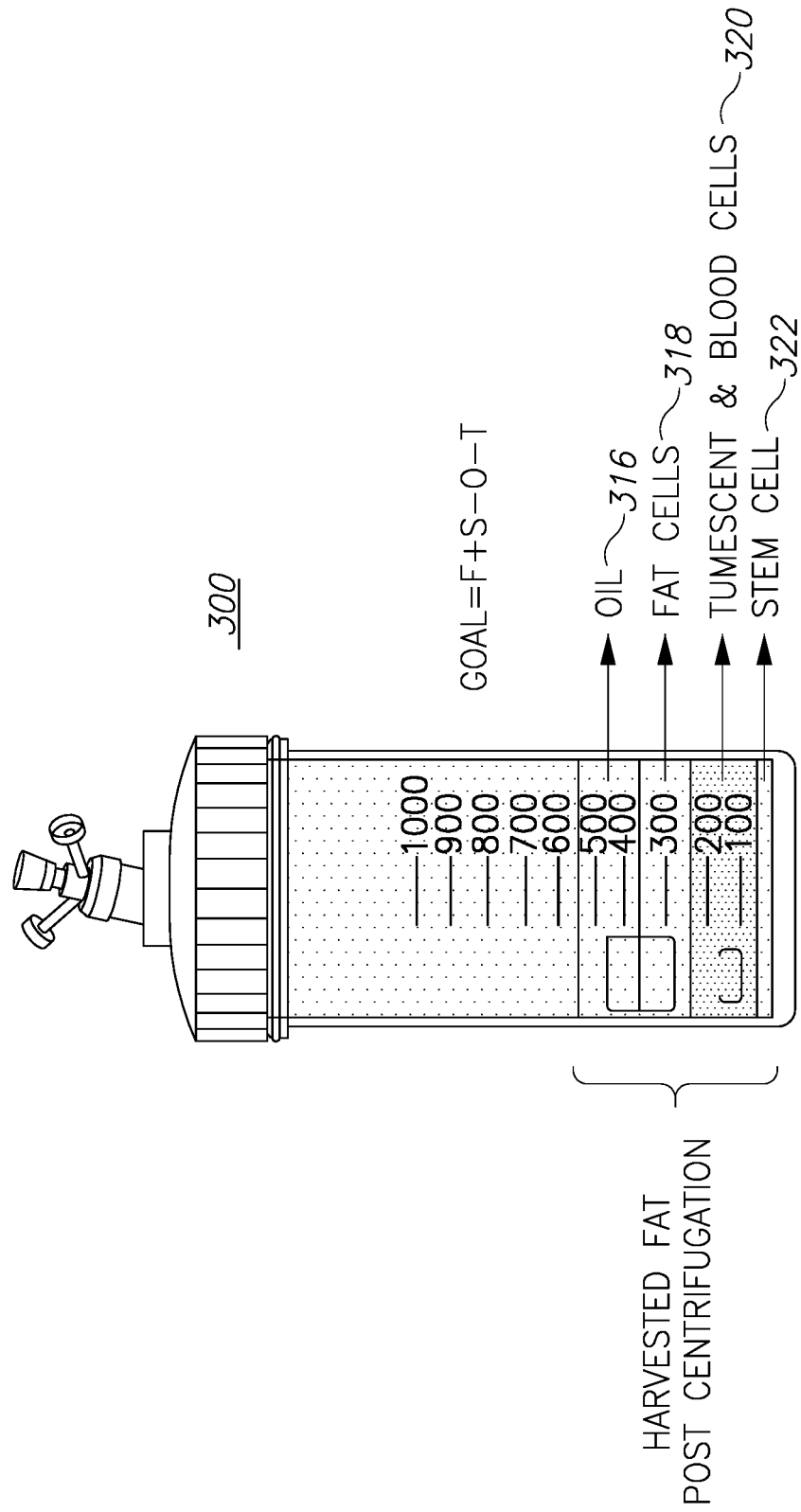
FIG. 7 illustrates the overall process for harvesting and separating adipose fat materials into its several components.

FIG. 7 shows a container 300 similar to that shown in FIG. 4. The "state" of container 300 shown in FIG. 7 is that after the adipose tissue had been introduced into the container and after the container has been manipulated, such as by spinning or centrifugation, so the tissue is separated into several components. These components may be: oils and lipids 316 (similar to oils components 16 in FIG. 3); fat cells 318 (18 in FIG. 3); tumescent and blood cells 320 (20 in FIG. 3); and stems cells or SVP 322 (22 in FIG. 3). As described above regarding FIG. 4, volume 33 is configured to hold both undesirable layers 16 and 20. As the inner most volume, volume 33 has more dimensional limitations and at the same time has to accommodate more material. In addition, the main container may be filled with harvested material and discharge processed material from its upper side rather than its bottom.

Therefore, an alternative four chambers container will now be described.

The four chambers container is formed by a four concentric barrels configured to move one relative to the others. A first volume may be created between the first and second barrel. A second volume maybe created between the second and third barrels. A third volume may be created between the third and fourth barrel and a fourth volume is defined by the fourth barrel.

Valve 330 is configured to open or close fluid communications from one volume to another. A tube connected to valve 330 is configured to control the valve and is also configured to allow the flow of harvested material into the first volume or processed material from the first volume from the top side of the container.

According to one example of this second embodiment, disclosed are three chambers which are designed to contain fluids and one "empty" air chamber which provides one degree of freedom to allow a relative movement of adjacent barrels so that volumes of relative adjacent volumes may be changed. More particularly, in this example, volumes 1, 2 and 4 are designed to hold fluids while volume 3, acts as an air pocket in between volume 2 and 4, to allow the movement of the third barrel relative to the second and fourth barrels. By this movement of barrel 3, from a position it contacts the upper surface of barrel 2 in FIG. 8b, to the position it contacts the lower surface barrel 4 in FIG. 8c, it cancels the third air volume and opens the second volume (which was nulled before). As will be explained below, this allows the movement of layer 318 into this second volume.

Once again, the goal is to remove the oil layer and the blood cell layers and be able to combine the fat cells and stem cells for reintroduction into the patient. FIGS. 8A through 8E illustrate the sequence of separation of adipose tissue components.

In FIG. 8, the container 300 includes a main volume (or container) 350 in which all the components 616, 318, 320 and 322 are located but separated as described herein. The container also includes a first inner volume (or container) 352 which provides an air gap, as well as a second inner volume (or container) 354 within first volume (or container) 352 into which components may be moved in and out.

FIG. 8A shows the part of the sequence in which the valve 330 attached to shaft 332 is opened so that the component 316 may be moved from the main volume 350 into second inner volume 354, as in FIG. 8B. Next, in FIG. 8C, the valve 330 is opened to allow component 318 to move into the first inner volume 352. This component 318 is the separated adipose tissue that will be reintroduced into the patient. Next, in FIG. 8D, the components in layer 320 are moved into the second inner volume 354 to join with components 316. These two components are not needed and may be discarded afterwards. Next, once the components in layer 320 are moved out of the main volume 320, the components in layer 318 may be reunited as in FIG. 8E with the components 322 for mixing together and reintroduction into the patient.

What is claimed is:

1. A method of capturing and separating adipose tissue components comprising:
   (a) providing a triple-chambered container; the triple chambered container comprising:
   a main container body defining therein a first chamber and having an opening at its distal end a main barrel formed and movable longitudinally within the first chamber, the main barrel defining therein a second chamber for receiving fluids, the main barrel further having a first apertured stopper at its distal end;

a second barrel formed within the main barrel, the second barrel defining a third chamber for receiving fluids, the second barrel being movable longitudinally within and with respect to the main barrel, the second barrel having a distal end with a second apertured stopper;

a shaft adapted to fit within the second barrel, the shaft being movable longitudinally within and with respect to the second barrel, the shaft having a distal end which is engageable and disengageable with the second apertured stopper in the second barrel;

a device for controlling a movement of the distal end of the shaft with the aperture of the second barrel; and, wherein the second chamber and the third chamber may be selectively moved to receive and discharge fluids with respect to one another;

wherein the method comprises:

(b) providing a volume of adipose tissue to the first chamber;

(c) centrifuging the container so that the adipose tissue is separated into four components;

(d) the four components being, in order proximally to distally: oils, fat, blood components, and adipose-derived stem cells;

(e) moving the oils into the third chamber by moving the shaft to disengage it from the aperture in the second apertured stopper and moving the main barrel in the direction of the distal end of the first chamber until the oils are contained in the second barrel;

(f) closing the second apertured stopper by engaging the shaft with the aperture in the second apertured stopper such that the oils are constrained to remain within the third chamber;

(g) moving the fat into the second chamber by moving the second barrel in a proximal direction, thus opening the first apertured stopper, then advancing the main barrel in a distal direction so that the fat enters into second chamber;

(h) closing the first apertured stopper with the second barrel such that the fat is constrained to remain within the second chamber;

(i) moving the blood components into the third chamber by moving the shaft to disengage it from the aperture in the second apertured stopper and moving the main barrel in the direction of the distal end of the first chamber until the blood components are contained in the second barrel with the oils;

(j) closing the second apertured stopper such that the blood components and the oils are constrained to remain within the third chamber; and, (k) moving the adipose-derived stem cells into the second chamber by moving the second barrel in a proximal direction, thus opening the first apertured stopper, then advancing the main barrel in a distal direction so that the adipose-derived stem cells enter into second chamber with the fat.

2. The method of claim 1, further comprising:

(l) moving the fat and the adipose-derived stem cells from the second chamber into the first chamber;

(m) closing the first apertured stopper after the fat and the adipose-derived stem cells have been moved into the first chamber; and, (n) moving the main barrel in a distal direction to expel the fat cells and the adipose-derived stem cells from the first chamber to outside the container for injection into a human body.

* * * * *